US006485430B1

United States Patent
Quinn et al.

(10) Patent No.: US 6,485,430 B1
(45) Date of Patent: Nov. 26, 2002

(54) THERMODILUTION CATHETER HAVING A SAFE, FLEXIBLE HEATING ELEMENT

(75) Inventors: Michael D. Quinn, Plano, TX (US); Mark L. Yelderman, Plano, TX (US)

(73) Assignee: Edwards LifeSciences Corporation, Irvine, CA (US)

( * ) Notice: Subject to any disclaimer, the term of this patent is extended or adjusted under 35 U.S.C. 154(b) by 0 days.

(21) Appl. No.: 08/603,550

(22) Filed: Feb. 21, 1996

Related U.S. Application Data

(63) Continuation of application No. 08/049,231, filed on Apr. 19, 1993, now Pat. No. 6,387,052, which is a continuation of application No. 07/647,578, filed on Jan. 29, 1991, now abandoned.

(51) Int. Cl.[7] .............................................. A61B 5/00
(52) U.S. Cl. ..................................... 600/505; 600/526
(58) Field of Search .................................. 128/692, 713, 128/736; 606/27–31; 600/505, 526, 545

(56) References Cited

U.S. PATENT DOCUMENTS

| | | | |
|---|---|---|---|
| 3,359,974 A | 12/1967 | Khalil | |
| 4,089,336 A | 5/1978 | Cage et al. | |
| 4,198,957 A | 4/1980 | Cage et al. | |
| 4,236,527 A | 12/1980 | Newbower et al. | |
| 4,240,441 A | * 12/1980 | Khalil | 128/700 |
| 4,507,974 A | 4/1985 | Yelderman | |
| 4,524,264 A | 6/1985 | Takeuchi et al. | |

(List continued on next page.)

OTHER PUBLICATIONS

Barankay et al, "Cardiac Output Estimation by a Thermodilation Method Involving Intravascular Heating and Thermistor Recording," Acta Physiologica Academiac Scientiarum Hungaricae, Tomus 38(2–3) pp. 167–173 (1970).*

(List continued on next page.)

Primary Examiner—Robert L. Nasser
(74) Attorney, Agent, or Firm—Oblon, Spivak, McClelland, Maier & Neustadt, P.C.

(57) ABSTRACT

A thermodilution catheter having a heating filament which is fabricated so as to be thin and flexible enough to avoid contact with the patient's blood. The heating filament is either inserted in a preformed catheter lumen, incorporated into a wall of the catheter body itself, or wrapped around the catheter body wall and surrounded by an external sheath. Generally, the covering of the heating filament is minimally thin so as to allow the heat from the heating filament to be transferred to the surrounding blood and to minimally increase the overall cross-sectional area. Since the heating filament does not directly touch the patient's blood, the outer surface may be made smooth so as to prevent inducement of blood clots. In addition, the heating filament may be maintained at a safe temperature by forming the heating element of a flexible material having a high temperature coefficient of resistance, low thermal capacitance and high thermal conductivity. Preferably, the temperature coefficient of resistance of the material forming the heater filament is greater than 0.001 $\Omega/\Omega\text{-}^\circ$ C. and the resistance of the heating filament is proportional or inversely proportional to its temperature. By monitoring this resistance, the application of power to the heating filament may be regulated to prevent overheating of the heating filament. Calibration techniques are also disclosed whereby a memory containing encoded calibration information is disposed within or connected to a connector of the catheter. This memory may also include a program segment used by a cardiac output computer having a cardiac output calculation program, whereby the portion of code stored in the memory must be input into the cardiac output computer before the determination of the cardiac output can be performed. As a result of these improvements, the invention enables the thermodilution cardiac output calculation to be performed quite safely and accurately in a clinical setting.

24 Claims, 5 Drawing Sheets

U.S. PATENT DOCUMENTS

| | | | |
|---|---|---|---|
| 4,814,586 A | * 3/1989 | Grise | 219/549 |
| 5,035,514 A | 7/1991 | Newman | |
| 5,057,105 A | 10/1991 | Malone et al. | |
| 5,087,256 A | * 2/1992 | Taylor et al. | 606/28 |
| 5,217,019 A | 6/1993 | Hughes | |
| 5,261,411 A | 11/1993 | Hughes | |
| 5,277,191 A | * 1/1994 | Hughes | 128/713 |
| 5,285,796 A | 2/1994 | Hughes | |
| 5,553,622 A | 9/1996 | McKown et al. | |
| 5,588,438 A | 12/1996 | McKown et al. | |

OTHER PUBLICATIONS

Journal of the American Society of Anesthesiologists, Inc., vol. 73, No. 3A, entitled: "Abstracts of Scientific Papers 1990 Annual Meeting", Sep. 1990, "Continuous Cardiac Output Measurement in ICU Patients." by Yelderman, Ramsey, Quinn, Paulsen, and McKown. The abstract is labeled in the upper right hand corner "A421."

Definition of "Chromel", p. 294 of the second edition of the "Dictionary of Scientific and Technical Terms," along with the title page and the copyright page.

Article by: H.H. Khalil et al.; entitled: "Measurement of cardiac output by thermal–dilution and direct Fick methods in dogs"; J. Appl. Physioi. 21(3): pp. 1131–1135; 1966.

Annals of Biomedical Engineering, vol. 17, pp. 61–73, 1989; entitled: "A Continuous Cardiac Output Computer Based on Thermodilution Principles"; R.A. Normann et al. (Received Feb. 1, 1988; Revised May 25, 1988).

IEEE Transactions on Biomedical Engineering, vol. BME–31, No. 5, May 1984; entitled: "Continuous Thermal Measurement of Cardiac Output"; James H. Philip et al.; pp. 393–400.

"Properties of Metals as Conductors"; p. E–85 of the CRC Handbook of Chemistry and Physics, $60^{th}$ Edition 1979–1980; along with the Title page and the copyright page.

Video cassette entitled: "INTERFLO" containing copy broadcasts of two televised news stories; one from Channel 5 and one from WFAA TV Channel 8.

Video Tape—Steve Griffin, InterFlo Medicine—Chamber of Commerce Interview dated Apr. 27, 1989.

* cited by examiner

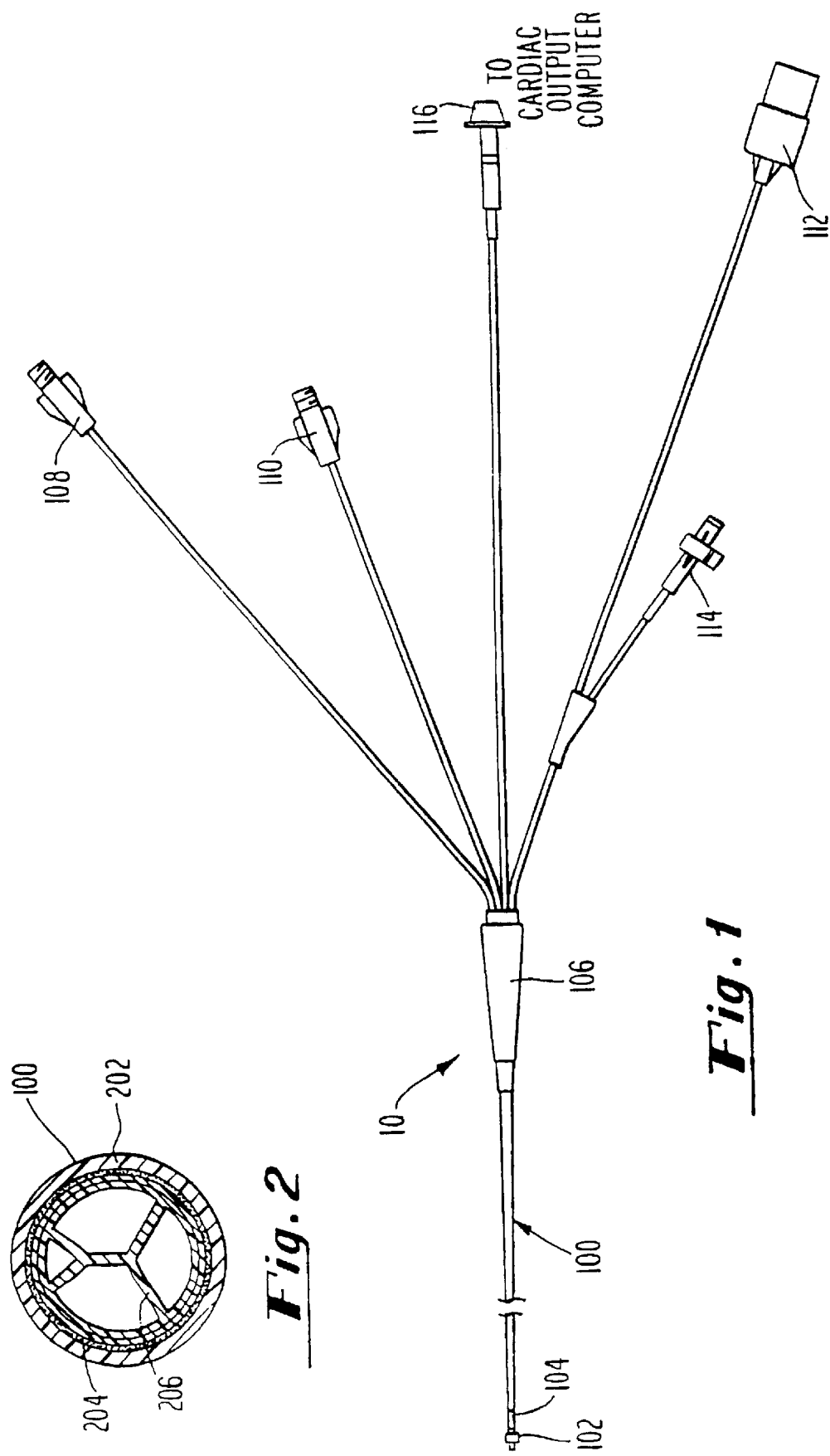

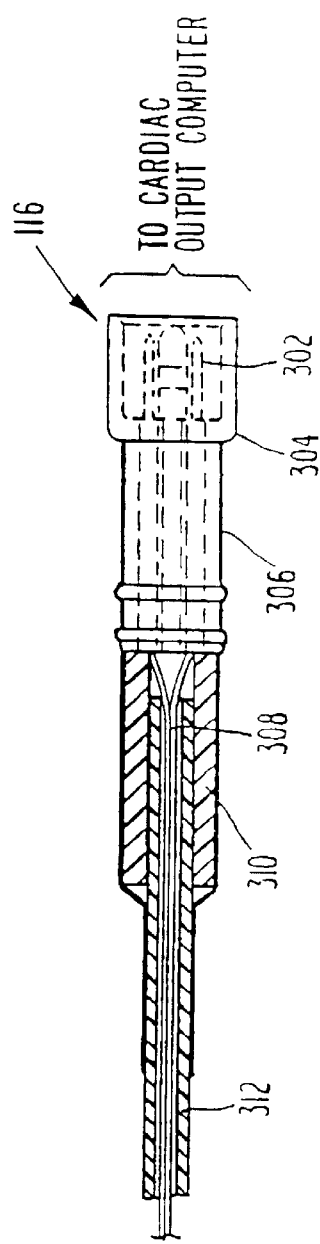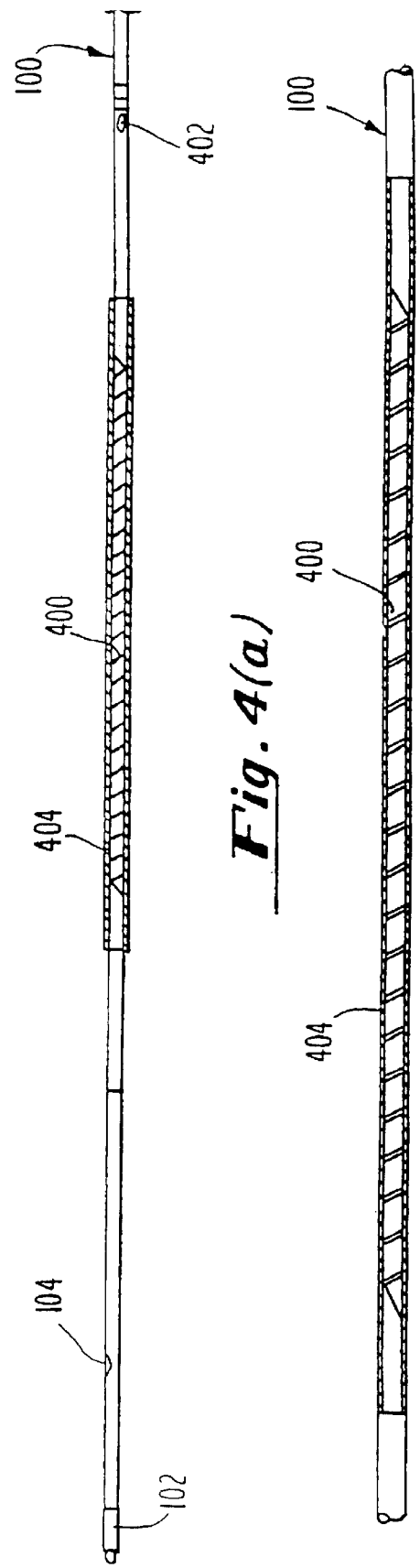

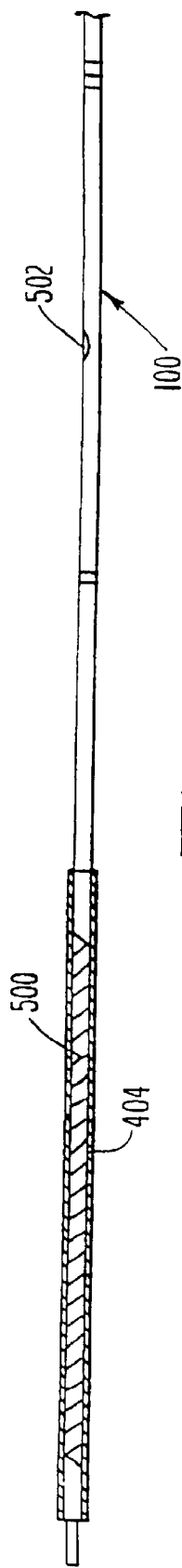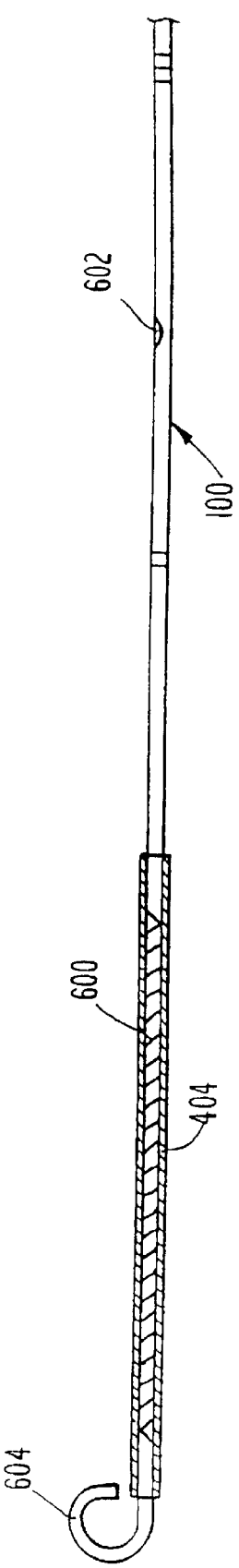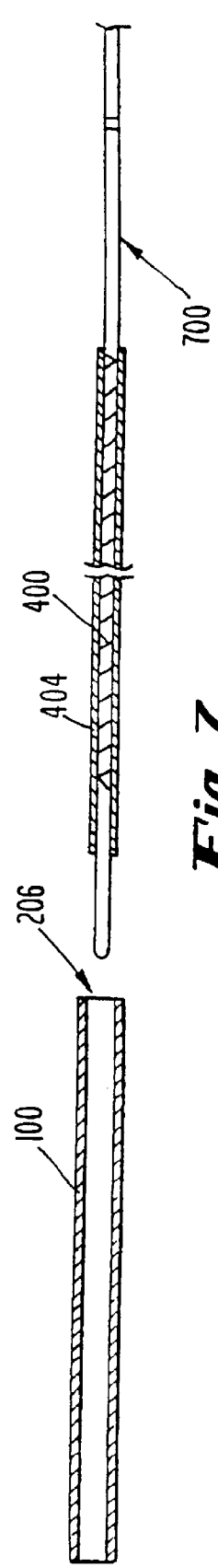

THERMODILUTION CATHETER HAVING A SAFE, FLEXIBLE HEATING ELEMENT

CROSS-REFERENCE TO RELATED APPLICATIONS

This is a continuation of application Ser. No. 08/049,231 filed Apr. 19, 1993, now U.S. Pat. No. 6,387,052 which is a continuation of application Ser. No. 07/647,578 filed Jan. 29, 1991, now abandoned.

BACKGROUND OF THE INVENTION

1. Field of the Invention

The present invention relates to a thermodilution catheter, and more particularly, to a thermodilution catheter having a flexible heating filament disposed therein for applying heat to the patient's blood for purposes of measuring cardiac output, volumetric blood flow, blood pressure, blood volume, blood components and the like.

2. Description of the Prior Art

As is well known, catheters have been developed for purposes of applying physiologic preparations directly into the blood streams of animals or humans or for measuring cardiovascular parameters such as cardiac output, blood pressure, blood volume, blood components and the like. Conventional catheters are made from various materials including plastics and are typically inserted into various body compartments, cavities and vessels to either deliver therapeutic agents, diagnostic agents, or to measure directly various physiologic parameters.

Numerous techniques have been disclosed in the prior art for measuring blood flow using catheters. For example, in U.S. Pat. No. 4,507,974, Yelderman describes a technique for measuring blood flow by applying a stochastic excitation signal to a system inlet and measuring the output signal at a downstream system outlet. The blood flow rate is then extracted by cross-correlating the excitation signal and the measured output signal. The problem addressed by systems of this type is particularly difficult since the physiologic blood vessels are elastic, thereby making classic fluid measuring techniques unacceptably inaccurate. In fact, because the blood vessels are elastic, blood flow cannot be measured unless (1) the physical heart dimensions are measured simultaneously with the blood velocity, (2) a technique is used which is independent of the vessel geometry or (3) a blood velocity technique is used which is calibrated by some other technique. Examples of each of these techniques may be found in the prior art.

For example, a prior art approach for simultaneously measuring blood velocity and vessel geometry is described by Segal in U.S. Pat. Nos. 4,733,669 and 4,869,263 and in an article entitled "Instantaneous and Continuous Cardiac Output Obtained With a Doppler Pulmonary Artery Catheter", *Journal of the American College of Cardiology*, Vol. 13, No. 6, May 1989, Pages 1382–1392. Segal therein discloses a Doppler pulmonary artery catheter system which provides instantaneous diameter measurements and mapping of instantaneous velocity profiles within the main pulmonary artery from which instantaneous cardiac output is calculated. A similar approach is taught by Nassi et al. in U.S. Pat. No. 4,947,852. A comparable ultrasound technique is disclosed by Abrams, et al. in U.S. Pat. Nos. 4,671,295 and 4,722,347 and in an article entitled "Transtracheal Doppler: A New Procedure for Continuous Cardiac Output Measurement", *Anesthesiology*, Vol. 70, No. 1, January 1989, Pages 134–138. Abrams et al. therein describe a technique whereby a piezoelectric ultrasound transducer is placed in the trachea of a patient in proximity to the aorta or pulmonary artery so that ultrasound waves may be transmitted toward the path of flow of blood in the artery and reflected waves received. The cross-sectional size of the artery is measured based upon the Doppler frequency difference between the transmitted and received waves. Imaging techniques such as x-ray or radio isotope methods have also been used.

Previous techniques which are geometry independent include an indicator dilution or dye dilution technique of the type first disclosed by Stewart in an article entitled "The Output of the Heart in Dogs", *American Journal of Physiology*, Vol. 57, 1921, Pages 27–50. Other such geometry independent techniques include a thermodilution technique as first described by Fegler in an article entitled "Measurement of Cardiac Output in Anesthetized Animals by a Thermo-Dilution Method", *Quarterly Journal of Experimental Physiology*, Vol. 39, 1954, Pages 153–164 and an ionic dilution technique as described by Geddes et al. in U.S. Pat. No. 4,572,206.

On the other hand, prior art techniques for measuring blood velocity which require a secondary calibration technique include a pulse contour technique of the type described by Schreuder, et al. in an article entitled "Continuous Cardiac Output Monitoring During Cardiac Surgery", *Update In Intensive Care And Emergency Medicine*, Berlin: Springer-Verlag, 1990, Pages 413–416. Another so-called "hot wire" anemometer or heated thermistor technique has been described, for example, by Tanabe, et al. in U.S. Pat. No. 4,841,981 and EP 235811 and by Sekii, et al. in U.S. Pat. No. 4,685,470 and WO 8806426.

The present invention relates to a geometry independent technique, namely, indicator dilution. In conventional indicator dilution techniques, different methods of indicator delivery may be used. For example, Khalil in U.S. Pat. No. 3,359,974 introduces indicator as a step increase and measures the resultant distal temperature change. Newbower, et al., on the other hand, discloses in U.S. Pat. No. 4,236,527 the technique of introducing the indicator as a sinusoid and measuring the distal wave attenuation. In addition, the indicator may be applied as an impulse so that the area under the resultant response may be measured as described by Normann in U.S. Pat. No. 4,576,182. Eggers, et al. in U.S. Pat. No. 4,785,823 similarly provide an impulse, but Eggers, et al. use high frequency energy to provide large heat fluxes to the blood without increasing the filament temperature. In addition, Petre describes in U.S. Pat. No. 4,951,682 an intra-cardiac impedance catheter which measures cardiac output based on changes in the electrical impedance of the blood in the right ventricle. By contrast, as described by Yelderman in the afore-mentioned U.S. Pat. No. 4,507,974, the indicator may be supplied according to a pseudo-random binary sequence and the distal response measured. Cross-correlation can then be performed between the input sequence and the output sequence, and flow is computed based upon the area under the cross-correlation curve. Each of these techniques may provide either an intermittent or a continuous measurement.

Although each of the above-mentioned techniques may use a variety of indicators, heat is the preferred indicator to be used in the clinical environment, for unlike other indicators, heat is conserved in the immediate vascular system but is largely dissipated in the periphery in one circulation time so as to eliminate recirculation and accumulation problems. On the other hand, if cold (negative heat) indicators are used, large amounts of cold may be used, for cold has relatively no deleterious effects on blood and surrounding tissues. However, when cold is used, it must be supplied in a fluid carrier such as saline since cold producing transducers are not readily economical or technically available at present. For example, such a technique is described by Webler in U.S. Pat. No. 4,819,655 and by Williams in U.S. Pat. No. 4,941,475, but the cold-based technique of Webler or Williams has significant clinical limitations in that the circulating fluid must be cooled to near ice temperature prior to input into the catheter and temperature equilibrium established, which takes a significant amount of time. In addition, the enlarged catheter segment containing the cooling elements may restrict blood flow. By contrast, if heat is used, a maximum heat infusion limitation is quickly reached since small increases in heat transducer temperature can have a deleterious effect on blood and local tissue. In fact, it can be inferred from the teachings of Ham et al. in "Studies in Destruction of Red Blood Cells, Chapter IV. Thermal Injury", Blood, Vol. 3, pp. 373–403 (1948), by Ponder in "Shape and Transformations of Heated Human Red Cells", J. Expo. Biol., Vol. 26, pp. 35–45 (1950) and by Williamson et al. in "The Influence of Temperature on Red Cell Deformability", Blood, Vol. 46, pp. 611–624 (1975), that a maximum safe filament surface temperature is probably about 48° C. Since the surface temperature of a heat transducer is a function of the blood flow velocity, the surface area and the heat flux, the optimum design is to maximize the heat delivered to the blood while minimizing the transducer surface temperature.

A heat transducer must satisfy several requirements if it is to be used clinically. Namely, the heat transducer or filament must be electrically safe. It also must only minimally increase the catheter cross-sectional area or diameter and must be made of materials which are non-toxic, which can be sterilized, and which can safely and easily pass through a standard introducer sheath. The heater must also be flexible so as not to increase the stiffness of the catheter body and must be capable of transferring the electrically generated heat to the surrounding blood without exceeding a safe filament surface temperature. Moreover, means must be present to continuously monitor the filament temperature to detect unsafe filament temperature and/or stagnant blood flow. However, prior art heater elements for catheters have not heretofore addressed these problems.

Prior art heater elements for thermodilution catheters have typically used simple resistive wire wound around the catheter. For example, Khalil discloses in U.S. Pat. No. 3,359,974 and Barankay, et al. disclose in an article entitled "Cardiac Output Estimation by a Thermodilution Method Involving Intravascular Heating and Thermistor Recording", Acta Physiologica Academiae Scientiarum Hungaricae, Tomus 38 (2–3), 1970, Pages 167–173, wrapping the wire around the catheter but describe no methods for securing the heater material to the catheter body. Normann, in U.S. Pat. No. 4,576,182, discloses a design similar to that of Khalil. However, such exposed or minimally required wire as used in these devices increases the catheter cross-section, thereby making it difficult for the catheter to pass through an introducer and providing a rough surface which may introduce local blood clot formation. In addition, such an arrangement provides no protection from fragments of the filament becoming dislodged and does not evenly dissipate the heat, thereby producing "hot" spots near the filament itself. It is thus desired to design a catheter heating filament which is electrically, mechanically and thermodynamically safe.

As noted above, although heat is a preferred indicator for dilution methods for measuring blood flow, the amount of heat delivered is limited or restricted by the maximal safe filament surface temperature. Although no absolute safe maximum filament temperature has been developed in the prior art, sufficient information is present in the literature to substantiate a reasonably safe maximum. For example, amongst blood, proteins and vessel tissue, red blood cells have been shown to be probably the most susceptible to higher temperatures. It is also well documented in the prior art that red blood cells can sustain an incubation temperature of 48° C. for up to one hour before developing significant abnormalities, as described by Williamson, et al. In any event, because the actual contact time of each red blood cell flowing past the heating filament is significantly less than several seconds, such a maximum of 48° C. is easily acceptable. A catheter heating filament can be designed to provide sufficient surface area to allow adequate heat infusion with a surface temperature below this maximum; however, changes in flow, such as sudden decreases or cardiac arrest, or changes in catheter position, such as becoming lodged against a vessel wall, may provide a local stagnant blood environment. Such stagnant environments may allow for surface temperatures which exceed these maximum limits and can thus cause harm if a method is not present for measuring filament temperature.

In addition, in prior art heating filaments for thermodilution catheters either the filament temperature has not been measured or the temperature is measured with a second thermometer. Such techniques obviously are unacceptable if a maximum safe temperature is to be maintained. Acceptable temperature sensing materials require a sufficiently high temperature coefficient of resistance to measure changes in temperature. Compositions of this type are described, for example, by Morris, et al. in an article entitled "Thin Film Thermistors", Journal of Physics Engineering: Scientific Instruments, Vol. 8, 1975, Pages 411–414. It is desired to develop a method for continuously measuring the filament temperature without the use of a secondary measuring transducer such as a thermistor or thermocouple of the type used in these prior art devices.

A classical prior art method of measuring fluid velocity uses a hot-wire anemometer. In accordance with this technique, a filament is heated with a constant power or at a constant heat flux and the resistance is measured. If a filament with a high temperature coefficient of resistance is used, the measured resistance can be used to directly calculate filament temperature, for the filament temperature is monotonically and inversely proportional to the fluid velocity. Such a technique has been previously described as a means for measuring blood velocity by Gibbs in an article entitled "A Thermoelectric Blood Flow Recorder in the Form of a Needle", Proc. Soc. Exp. Biol. & Med., Vol. 31, 1933, Pages 141–146. However, as noted by Gibbs in that article, such a technique has been limited to peripheral vessels and cannot give absolute blood volumetric flow rates, only velocity. It is desired to adapt such techniques to thermodilution measurements to prevent localized overheating of the blood.

As noted above, previous heating elements for thermodilution catheters have generally used wire and wrapped it around the catheter. However, such an approach provides for uneven heat densities on the catheter since the wire tends to be hot and the space between the wire cooler. A more uniform material is desired which allows for more even heat densities and the elimination of "hot" spots. This is not possible with wire, for wire, even very small gauge wire, provides a larger cross-section for the catheter than necessary since there is unused space between the wire even when the wire is wound very compactly. A more uniform material would allow for a better distribution of the same quantity of heat with only a small increase in catheter cross-section. It is thus desirable to develop a filament material which minimally increases a cross-sectional area of the catheter and which provides a more uniform filament heat flux.

Accordingly, there are numerous problems with prior art thermodilution catheters which render them either inaccurate or unacceptably unsafe for use in the clinical environment. There is thus a long-felt need in the art for a filamented thermodilution catheter which overcomes these limitations of the prior art so as to allow production of a safe, accurate thermodilution catheter. The present invention has been designed to meet this need.

SUMMARY OF THE INVENTION

A safe, accurate thermodilution measurement may be made in accordance with the present invention by using a catheter having a heating filament which resides internal to the catheter body, either in a preformed catheter lumen or beneath an outer sheath, and which preferably does not directly contact the blood. The heating filament is preferably made of a thin, flexible material which may be wrapped either on the exterior of the catheter body wall and then covered by an external sheath material so that the heating filament material is not exposed to the blood or on the outer surface of a supporting sheath inserted into the catheter lumen. The heating filament so designed supplies a quantity of heat to the flowing blood which is used for measuring the volumetric blood flow using an indicator dilution equation. During use, the filament temperature is preferably measured simultaneous with the thermodilution measurement without the use of a second measuring transducer—not to calculate velocity, but so that a safe filament temperature may be maintained. This is accomplished in a preferred embodiment by forming the heating filament of a material which has a resistance proportional or inversely proportional to its temperature.

In addition, the invention allows determination of blood flow using thermodilution techniques in clinical situations which were impossible using the classic bolus thermodilution method. For example, in applications such as measuring left ventricular blood flow or measuring hepatic blood flow, the natural blood flow is "retro grade", i.e., the blood flows from the distal end of the catheter toward the proximal portion. In this situation, it is necessary to place the thermal filament at the distal tip and locate the detection thermistor or thermocouple in a proximal location. The classical thermodilution catheter cannot be used in such a case since it is necessary to have the indicator flow under and past the detection thermistor or thermocouple, which in the case of "retro grade" blood flow induces an enormous amount of cross-talk and error. However, if an electrical filament is used, such as in the present invention, the electrical current can be passed under and past the detection thermistor or thermocouple without inducing thermal cross-talk and error.

Thus, in accordance with the invention, a thermodilution catheter is provided which comprises:
a flexible tubular catheter member adapted for introduction into a blood vessel of a patient;
a flexible heating filament disposed with respect to the catheter member so as not to touch the patient's blood when the catheter member is inserted into a blood vessel, the heating filament applying a predetermined quantity of heat to blood in the blood vessel; and
temperature detecting means for detecting downstream temperature variations of the blood as a result of application of the predetermined quantity of heat to the blood.

In accordance with a preferred embodiment of the invention, the catheter member comprises a substantially cylindrical body wall portion and an outer sheath, where the heating filament is wrapped in a thin layer about the body wall portion of the catheter member and enclosed by the sheath. The sheath may be a flexible material formed by extrusion or blow molding or a flexible material which shrinks to form-fit the heating filament and the body wall portion when a sufficient quantity of heat is applied thereto. A layer of material with high thermal conductivity may also be disposed about the heating filament so as to create a more uniform surface temperature. The body wall portion may also have a reduced diameter in the region where the heating filament is wrapped therearound such that the resulting total diameter in that region is approximately equal to the diameter of the body wall portion in other regions. In some embodiments, the sheath material may actually contain the resistive heating material so as to form one element, thereby eliminating the need for a separate filament and sheath.

The heating element is placed upstream or downstream from the temperature detecting means depending upon whether "retro grade" or flow-directed measurements are made. Also, at least one set of electrical leads is attached to the heating filament at a first end thereof so as to apply power to the heating filament and is attached at a second end thereof to a cardiac output computer which applies an appropriate power signal to the electrical leads when the predetermined quantity of heat is to be applied to the blood. Typically, the cardiac output computer continuously monitors both current and voltage delivered to the catheter filament. From the product of current and voltage, the delivered heat may be computed, and from the ratio of voltage to current, the actual filament temperature may be calculated.

In accordance with another aspect of the invention, calibrating means are provided for calibrating both the heating filament and the temperature detecting means. Preferably, the calibrating means comprises a Read Only Memory (ROM) contained within the catheter member for storing calibration information for at least one of the heating filament and the temperature detecting means, as well as any other necessary information. Such calibration information may further include heating filament resistance at a given temperature, heating filament heat transfer efficiency, temperature coefficient of resistance and thermistor information. Moreover, the ROM may be connected to a cardiac output computer so as to pass a program segment, stored in the ROM, of a program used by the cardiac output computer to calculate cardiac output of the patient, whereby calculation of the patient's cardiac output cannot commence until the cardiac output computer is connected to the ROM and the program segment transferred to the cardiac output computer.

In accordance with another preferred embodiment of the catheter apparatus of the invention, the catheter member has at least one lumen through which the heating filament is removably inserted. In such an embodiment, the heating filament is wrapped in a thin layer about a substantially cylindrical supporting member such that the combination has an outer diameter which is approximately equal to an inner diameter of the lumen through which it is inserted. Preferably, the heating filament is approximately 5 to 10 centimeters in length and is disposed approximately 10 centimeters from the temperature detecting means.

In accordance with another aspect of the invention, the heating filament is comprised of a material having a high temperature coefficient of resistance, whereby resistance of the heating filament is inversely proportional to its temperature (i.e., it has a negative temperature coefficient of resistance). This aspect of the invention enables power to the heating filament to be reduced when resistance of the heating filament exceeds a predetermined resistance amount, which is reached when the temperature of the heating filament reaches approximately 52° C. A material suitable for the heating filament thus has a temperature coefficient of resistance greater than $0.001\Omega/\Omega-°$ C. Also, such a material preferably has a low thermal capacitance and high thermal conductivity. Preferred heating filament materials include an alloy of approximately 70% nickel and 30% iron and an alloy of approximately 29% nickel, 17% cobalt and 54% iron.

The invention further relates to a method of applying heat to blood in a blood vessel of a patient for purposes of conducting a thermodilution measurement. Such a method in accordance with the invention comprises the steps of:

inserting a flexible tubular catheter member having a heating element disposed beneath an outer sheath thereof into the blood vessel of the patient so as not to directly expose the heating element to blood in the blood vessel;

applying power to the heating element so as to generate a predetermined quantity of heat; and applying the predetermined quantity of heat through the catheter member to blood in the blood vessel.

A preferred embodiment of such a method in accordance with the invention preferably comprises the further steps of:

forming the heating filament of a material having a high temperature coefficient of resistance whereby resistance of the heating filament is proportional or inversely proportional to its temperature and having a low thermal capacitance and a high thermal conductivity; and reducing power to the heating filament when resistance (and consequently the temperature) of the heating filament exceeds a predetermined resistance amount (temperature). These steps prevent localized overheating and thus help assure patient safety.

Another embodiment of a method in accordance with the invention for applying heat to blood in a blood vessel of a patient for purposes of conducting a thermodilution measurement comprises the steps of:

inserting a flexible tubular catheter member into the blood vessel of the patient;

removably inserting a flexible heating filament through a lumen of the catheter member;

applying power to the heating filament so as to generate a predetermined quantity of heat; and applying the predetermined quantity of heat through the catheter member to blood in the blood vessel.

Such methods in accordance with the invention also preferably comprise the further step of calibrating the heating filament using a memory disposed at a proximal end of the catheter member, where the memory stores calibration information including heating filament resistance at a given temperature and/or heating filament heat transfer efficiency and thermistor information. This memory is then connected to a cardiac output computer so that the cardiac output calculation can use the calibration information stored in the memory.

Pirating of the catheter of the invention may also be prevented by performing the thermodilution measurement in accordance with the following steps:

inserting a flexible tubular catheter member having a flexible heating filament disposed beneath an outer sheath thereof into a blood vessel of a patient such that the heating filament does not directly contact the patient's blood;

applying power to the heating filament so as to generate a predetermined quantity of heat;

applying the predetermined quantity of heat through the catheter member to blood in the blood vessel;

detecting downstream temperature variations of the blood as a result of application of the predetermined quantity of heat to the blood;

storing in a memory disposed at a proximal end of the catheter member a program segment of a program used by a cardiac output computer to calculate cardiac output of the patient;

connecting the memory to the cardiac output computer;

transferring the program segment to the program of the cardiac output computer; and calculating the cardiac output of the patient in accordance with the program including the program segment and the detected temperature variations.

Thus, by providing a heating filament which is minimally thin, heat from the filament may be transferred to the surrounding blood in accordance with the invention without significantly increasing the overall cross-sectional area of the catheter. Also, by providing a surface coating for the resulting catheter which has no rough areas to induce blood clot formation, the thermodilution catheter of the invention may be more safely used in clinical settings. Moreover, by monitoring the heating filament temperature, localized overheating may be prevented. Other elements or drugs, such as heparin, antibiotics and the like may be added to the filament sheath to reduce the possibility of any complications as a result of the measurements using the catheter of the invention.

BRIEF DESCRIPTION OF THE DRAWINGS

The above and other objects and advantages of the invention will become more apparent and more readily appreciated from the following detailed description of the presently preferred exemplary embodiments of the invention taken in conjunction with the accompanying drawings, of which:

FIG. 1 is an overall perspective view illustrating the proximal end of a catheter for measuring cardiac output in accordance with the present invention;

FIG. 2 illustrates a cross-sectional view of the catheter of FIG. 1 showing the filament lead lumen which receives the heating filament leads and/or heating element in accordance with the invention;

FIG. 3 illustrates a detail view of the heater connector 116 of the catheter of FIG. 1;

FIG. 4(a) illustrates a first embodiment of a distal end of the catheter of the invention for use in flow-directed measurement, whereby the heating filament is wound about a body wall portion of the catheter and is enclosed within an outer sheath;

FIG. 4(b) illustrates a modification of the first embodiment whereby the heating filament is flush with the adjacent section of the catheter body so as to prevent an increase in the catheter cross-section;

FIG. 5 illustrates a second embodiment of a distal end of the catheter of the invention for use in retro grade measurement, whereby the heating filament is wound about a body wall portion of the catheter and is enclosed within an outer sheath;

FIG. 6 illustrates a third embodiment of a distal end of the catheter of the invention for use in retro grade measurement, whereby a "pigtail" tip is provided to prevent blood vessel rupture;

FIG. 7 illustrates an embodiment whereby the heater element and its supporting sheath are inserted into the lumen of the catheter of FIG. 1;

DETAILED DESCRIPTION OF THE PREFERRED EMBODIMENTS

Figure 8:
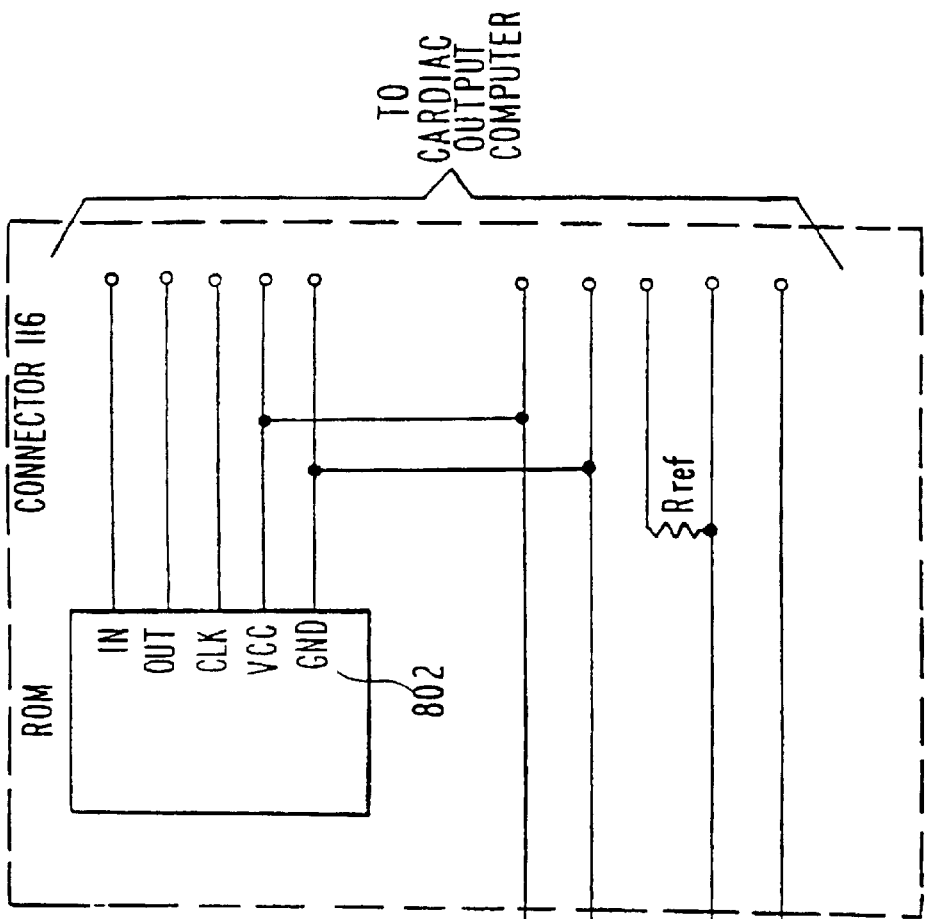
FIG. 8 illustrates a calibration circuit having a ROM in accordance with a preferred embodiment of the invention.

A system with the above-mentioned beneficial features in accordance with presently preferred exemplary embodiments of the invention will be described below in detail with reference to FIGS. 1–8. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

A detailed description of intra vascular catheters is not given herein, for the features of different types of catheters, namely flow-directed pulmonary artery catheters, left ventricular angiography catheters, and the like are well known to those familiar to the art. Some unique features of such catheters are described by way of example in U.S. Pat. Nos. 3,746,003; 3,634,924; 3,995,623; 4,696,304; 4,718,423; and 4,721,115.

FIG. 1 illustrates a proximal end of a catheter arrangement 10 in accordance with a first embodiment of the invention. As shown, the catheter arrangement 10 comprises a flexible catheter body portion 100 which is adapted for insertion into a blood vessel of a patient and is formed of a non-toxic material such as polyvinyl chloride (PVC). The catheter body portion 100 is also preferably coated with heparin to prevent blood clot formation. At a distal tip of the catheter body portion 100, an inflatable balloon 102 is provided for a flow-directed measurement so that the catheter arrangement 10 may be inserted into the right ventricle of the heart using the customary flow-directed insertion technique. Within a couple of centimeters of the balloon 102 is disposed a temperature sensing device such as a thermistor or thermocouple 104 for measuring the temperature of the flowing blood. This measurement is then used in the thermodilution volumetric blood flow calculation in accordance with known techniques, such as those described in co-pending patent application Ser. No. 07/510,897 to McKown et al. As shown in FIG. 1, the catheter body portion 100 for insertion into the blood vessel preferably has a length of, for example, 112 centimeters so that it is long enough to be "floated" into the right ventricle of the patient's heart using the flow-directed insertion technique. Insertion may thus be accomplished at bedside without the requirement of fluoroscopy.

At a proximal end of the catheter body portion 100 is provided a catheter body junction 106 through which devices such as a PA distal lumen hub 108, a proximal injectate lumen hub 110, a thermistor or thermocouple connector 112, a balloon inflation valve or stopcock 114, and a heater connector 116 may be inserted into respective filament lead lumens of the catheter body portion 100. In particular, as shown in FIG. 2, the catheter body portion 100 of the invention may comprise an outer layer 202 and an intermediate layer 204 which adheres the outer layer 202 to body wall portion 206 of catheter body portion 100. As shown, body wall portion 206 separates the internal area of catheter body portion 100 into one or more lumens for accepting the peripheral devices 108–116. As will be appreciated by those skilled in the art from the following description, one of the lumens permits leads from heater connector 116 to communicate with a downstream heating filament disposed within or about the catheter body portion 100. Although multiple lumens are shown, there is no reason that different leads cannot share a common lumen.

In accordance with the invention, the heater connector 116 communicates with a cardiac output computer so as to receive power signals for controlling the heating filament. Connector 112 forwards temperature changes measured by the thermistor or thermocouple 104 back to the cardiac output computer for calculation of the cardiac output in accordance with a known thermodilution technique. A presently preferred thermodilution technique is that described in co-pending patent application Ser. No. 07/510,897, to McKown et al. and assigned to the present Assignee. That patent application discloses a cardiac output computer which utilizes an improved stochastic technique from that disclosed by Yelderman in U.S. Pat. No. 4,507,974, for applying heat to the blood stream and evaluating the results in accordance with a cross-correlation of the input with the measured output. The disclosure of that application is hereby incorporated by reference as if set forth entirely herein.

The heater connector 116 is shown in more detail in FIG. 3. As shown, heater connector 116 comprises electrical connector 302 within a plug portion 304 for electrically communicating with the cardiac output computer. The electrical connector 302 communicates through electrical connections in casing 306 with heater wire leads 308. Heater wire leads 308 transverse the length of the support casing 310 and the supporting sheath or heater wire lumen 312 so as to electrically communicate with the heater filament as will be described below. The supporting sheath 312 is preferably made of teflon so as to be flexible yet strong. In accordance with the invention, the supporting sheath 312 supporting the heater wire leads 308 is inserted into a lumen of the catheter body portion 100 to facilitate electrical connection to the heating element. Electrical leads may be similarly "fished" through a lumen to connect to thermistor or thermocouple 104. A more complex connector will be described below with respect to FIG. 8.

FIG. 4(a) illustrates the manner in which the heating filament 400 is wrapped about the outer layer 202 of the catheter body portion 100 in accordance with a first embodiment. As shown, the heating filament 400 is formed so as to be very thin and flat so that it can be wrapped in a non-overlapping manner about the outer layer 202. As shown, an injectate or pacing port 402 may also be provided proximal to heating filament 400. The heating filament 400 is preferably wrapped to extend approximately 5 to 10 centimeters along the outer layer 202 and is disposed so as to be approximately 14 centimeters from the distal tip having balloon 102 of the catheter body portion 100. The heating filament 400 is then surrounded by a thin outer sheath 404 to prevent the heating filament 400 from directly contacting the patient's blood.

Generally, the heating filament 400 is printed on a substrate as a sandwich. The substrate of the heating filament consists of a thin material that is capable of being incorporated into a filament material which is preferably flexible and has the ability to bond with an adhesive. It must also have good heat transfer properties which allow for the conduction of the filament generated heat to the exterior of the outer sheath 404 so as to be applied to the blood. An additional layer of material with high thermal conductivity (e.g., metal foil) may be added to the heater sandwich to help create a more uniform surface temperature. The filament substrate materials of the invention include, but are not limited to, Mylar and Kapton. On the other hand, the filament material, which is adhered to the substrate, can be any material which has a high temperature coefficient of resistance, i.e. greater than $0.001\Omega/\Omega$-° C., and low thermal capacitance and high thermal conductivity. The material must be capable of being incorporated into the filament substrate and must be capable of being fabricated in thin layers so as to form a sandwich (e.g. Kapton—adhesive—filament metal—adhesive—Kapton). Alloys for the filament material include, but are not limited to, an alloy of 70% nickel and 30% iron or an alloy of 29% nickel, 17% cobalt and 54% iron.

An adhesive material must be selected which is capable of binding to both the outer sheath 404 and the catheter body portion 100, and to the filament substrate, or in some applications, directly to the filament material. The adhesive must be capable of being applied in a thin, even layer, must be non-toxic, must not weaken with time, must tolerate heat from the filament, must tolerate continual flexing, and must bind well in a wet environment (i.e., blood). Such adhesives include, but are not limited to, pressure sensitive adhesives such as Densil.

Figure 10:
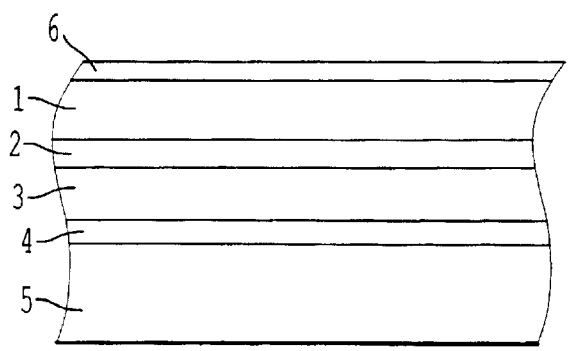
FIG. 10 illustrates a sandwich structure providing a substrate for the filament metal.

FIG. 10 shows a sandwich structure having a filament substrate material 5 upon which is an adhesive material 4. A filament metal layer 3 is held to the filament substrate material 5 by the adhesive layer 4. Another adhesive layer 2 that is above the filament metal holds the upper layer 1 to the filament metal 3. An additional layer 6 having a high thermal conductivity helps create the more uniform surface temperature.

In another embodiment, the adhesive, the outer sheath material and the electrical resistive components may all be incorporated into one material. The electrical leads are then connected to the material, which is formed as a sheath or wrapping material and applied directly to the outer layer 202 of the catheter body portion 100 or incorporated during the manufacturing process directly into the outer layer 202 of the catheter body portion 100.

In accordance with the invention, the thin heating filament materials of the invention may be spirally wound around the catheter body portion 100 to form a heating filament 400 as just described. Although the filament substrate or filament heater material may be exposed directly to the blood environment as in the prior art devices, in accordance with the invention the filament substrate and/or filament material are preferably enclosed, surrounded by, or incorporated within an outer sheath 404 for assuring that fragments of filament or filament substrate do not become dislodged into the blood environment. Moreover, by providing a covering material or outer sheath 404, the exterior of the catheter may be made smoother and hence more comfortable for the patient during insertion into the blood vessel. Of course, this structure is made possible because the above-mentioned heater filament material may be formed into a very thin filament which may be non-overlappingly wound about the catheter body portion 100. However, the sheath 404 must also be very thin and flexible and is preferably an adhesive applied by any of a number of techniques over the filament or filament substrate. Such adhesives include, but are not limited to, Master Bond EP37. The resulting catheters are then preferably coated with heparin to prevent blood clot formation.

Regardless of the type of filament material used or the number of layers of materials or sandwich composition, the catheter body may be reduced in diameter in the region where the filament sandwich is wound, as shown in FIG. 4(b). The reduction in catheter body diameter is made such that, when the filament sandwich is added, the resulting total diameter in the region of the heating filament is equivalent to the diameter of the adjacent catheter body portion without the filament material. This achieves a uniform transition to the region of the catheter filament, thereby eliminating problems associated with insertion, removal and thrombus formation in regions of irregularities.

In accordance with the invention, a particularly attractive method for applying the sheath 404 is to use a flexible sheath material which can be applied over the filament, filament substrate, and filament-to-catheter body adhesive. Preferably, a material is used which has an appropriate modulus of elasticity and elongation. The material may be fabricated by a technique such as extrusion so that its resting lumen diameter is less than that of the catheter filament sub-assembly. The sheath material or "tube" may then be expanded using a "vacuum expander" to a size larger than the catheter and attached filament sub-assembly. The catheter and sub-assembly may then be passed into the vacuum expander containing the expanded sheath, positioned in place, and then the vacuum released. The sheath then shrinks, reduces or collapses around the filament sub-assembly so as to maintain a certain tension with the underlying components. Preferably, the vacuum expander contains a chamber which allows for the placement of the sheath material so that the ends of the sheath material may be secured to form a closed chamber between the outer wall and ends of the sheath material and the surrounding chamber. The chamber dimensions may be such as to allow for the expansion of the sheath to a size which is large enough to accept the passage of the catheter body portion 100 and the attached filament sub-assembly. The sheath then may be expanded by applying a vacuum to the chamber and/or positive air pressure to the inside of the sheath. Expansion of the sheath may also be improved by applying heat to the expansion chamber. Conversely, a blow molding technique may be used in accordance with known techniques. A material which may be manufactured to have such a thin wall, an appropriate modulus of elasticity, and an appropriate elongation includes, but is not limited to, Tecoflex™.

Another method of sheath application in accordance with the invention utilizes shrink material. The sheath may thus be fabricated to be slightly larger than the catheter body portion 100 and the attached filament sub-assembly. It is then applied without the vacuum expander, and when the sheath material is situated in the proper location, it is reduced in size by the application of heat. Again, the proper wall thickness and beginning dimensions are chosen such that, following the reduction in size, appropriate tension is maintained with respect to the underneath filament sub-assembly.

Preferably, as described above, the cylindrical heating filament 400 is approximately 10 centimeters in length and is wrapped about the outer wall 202 of the catheter body portion 100 beginning distally about 15 centimeters from the distal tip of the catheter. Then, when the catheter is positioned with the distal tip in the pulmonary artery during a flow-directed measurement, a proximal fluid infusion port of the catheter will lie in the right atrium of the heart or superior vena cava while the distal fluid infusion port will lie in the right ventricle.

An alternative embodiment of the invention for measuring blood flow in a "retro grade" fashion, such as in the hepatic vein, is shown in FIG. 5. As shown, the heating filament 500 and the thermistor or thermocouple 502 are in reversed positions on the catheter body portion 100 because of the reversed blood flow direction. Since this type of catheter is inserted into the blood vessel against the blood flow, insertion generally requires the use of fluoroscopy for directing the catheter into place for measurement. Since the embodiment of FIG. 5 is not a flow-directed catheter, a balloon at the distal tip is not used.

The alternative embodiment of FIG. 6 may also be used for measuring blood flow in a "retro grade" fashion, as in the left ventricle of the heart, whereby the heating filament 600 and thermistor or thermocouple 602 are in reversed positions on the catheter body portion 100 as in the embodiment of FIG. 5. As in the FIG. 5 embodiment, insertion generally requires fluoroscopy and a balloon tip is not used. However, a pigtail tip 604 is preferably used in this embodiment to prevent vessel rupture.

During operation, since the heating filament formed as described above is used primarily to insert heat into the blood stream, it will rise to a temperature higher than the surrounding environment. Thus, it is necessary to know the filament temperature since, should the temperature become excessive, damage could result to the surrounding blood and tissues. Normally, a second temperature sensing device such as a thermistor or thermocouple would need to be embedded next to the filament to measure its temperature. However, by using a filament material which has a high temperature coefficient of resistance as herein described, not only can it be used as a heat supplier, but it can also serve as its own temperature sensing device. For example, resistance of any material is measured as follows:

$$R = \frac{\rho \cdot l}{A},$$

where

ρ is the resistivity, l is the length, and

A is the cross-sectional area.

Then:

$$\Delta R = \frac{\Delta \rho \cdot l}{A},$$

and if α, the mean temperature coefficient of resistivity, is defined as:

$$\alpha = \frac{1}{\rho} \cdot \frac{\Delta \rho}{\Delta T},$$

where

Δρ is the change in the coefficient and

ΔT is the change in temperature, then:

$$\Delta T = \Delta R \frac{A}{l \cdot \alpha \cdot \rho}.$$

Then, by measuring the current (i) and the voltage (v), both delivered power and resistance of the filament can be simultaneously measured as:

$$\frac{\Delta v}{\Delta i} = \Delta R.$$

The heating filament 400 of the invention typically consists of a cylindrical design which is approximately 5–10 centimeters in length. Heater wire leads 308 are attached to the heating filament 400, and the heating filament 400 is placed at the desired distance from the thermistor or thermocouple 104 (10 cm in FIGS. 4(a) and (b)). Then, as previously described, the heat transfer is such that the heat passes from the heater filament 400 through the outer sheath 404 into the blood. Of course, the heating filament 400 must be flexible such that it does not increase the stiffness of the catheter body portion 100.

In accordance with another embodiment of the invention, as shown in FIG. 7, the heating filament 400 may be made as a mobile module supported by a flexible supporting member 700 which can be inserted or withdrawn from the catheter lumen after the catheter has been inserted into the patient. This has the advantage that the catheter can be inserted into the patient when it is not known whether measurement of blood flow is required. Should the measurement of blood flow become desirable, the mobile filament module can be inserted and the measurement started. This feature of the invention is particularly helpful in a clinical setting, for although pulmonary artery catheters were originally designed to measure distal pressure, more features have been added such as bolus thermodilution cardiac output measurements, cardiac pacing and mixed venous saturation. Thus, the clinical problem now is to know which catheter to use, for not all patients require all measurement modalities.

The invention is thus designed as a pulmonary artery catheter which has one or more ports and/or lumens which will accept the particular modules (as shown in FIG. 1) for a particular measurement modality. For example, for a 4-lumen catheter of the type shown in cross-section of FIG. 2, one lumen may be dedicated to measuring distal catheter pressure, one lumen may be dedicated for distal balloon inflation and passage of two distal thermistor or thermocouple leads, one lumen may be dedicated to proximal fluid infusion the fourth lumen may be left open. Moreover, another lumen may receive a module for measuring mixed venous oxygen saturation including a fiber optic bundle. Other modules may be designed at the user's discretion.

During use, the pulmonary artery catheter of the invention (with the vacant lumen) is inserted in the usual and customary fashion. After insertion, if so desired, the physician or the user may electrically pace the heart by passing a modulus or wire through the vacant catheter lumen so as to connect the proximal end of the wire to the appropriate electronics. Such a concept of a removable pacing wire has been previously described by Swendson, et al. in U.S. Pat. No. 4,759,378, for example. On the other hand, if the measurement of mixed venous saturation is desired, the pacing wire modules would be removed and a fiber optics modulus inserted in the vacant lumen for measuring mixed venous saturation, and the proximal end of the fiber optics would be attached to the appropriate electronics. Such fiber optics techniques for measuring mixed venous saturation are described by Willis, et al. in U.S. Pat. No. 4,718,423, for example. However, the fiber optics technique taught by Willis, et al. is not removable; therefore, if cardiac output is desired, the vacant lumen must be replaced with the thermal transducer filament or other apparatus modulus for performing cardiac output measurement. Of course, the scope of the invention is not limited to just these modalities, but includes any modalities which could be used at the user's discretion.

Thus, in accordance with the invention, the heating filament 400 is placed either around the catheter body portion 100 but within an outer sheath 404 or is placed within the catheter body portion 100, namely, in a lumen thereof. In either case, the heating filament 400 does not directly contact the patient's blood. This is in marked contrast to previous embodiments where in the heating elements are generally placed on the exterior of the catheter or the filaments are used as unattached free-floating pieces. Instead, in accordance with the present invention the heating filament 400 is placed such that the heat transfer properties of the catheter body portion 100, the outer sheath material and heating filament material allow the transmission of heat to the exterior environment, namely, the blood stream. Such an arrangement has significant implications since an internally placed heating filament reduces the probability of harmful blood clot formation, electrical leakage currents, or unusually high filament blood contact temperatures.

When a thermodilution catheter in accordance with the invention is connected to a cardiac output computer via heater connector 116, an electrical current is applied to the heating filament in the form of pulses. When the heating filament is activated, an approximate average of 7.5 watts of power may be delivered to the heating filament. During operation, as described above, the cardiac output computer may continuously measure and monitor the filament temperature so as to limit the peak filament temperature to a maximum of 52° C. (which corresponds to a peak surface temperature of about 48° C. and an average surface temperature of about 44° C., depending upon the material composition and thickness). For example, in the event the heating filament temperature exceeds 52° C. for more than, say, 15 seconds at full power, the delivered heating filament power is reduced. Then, if the heating filament temperature exceeds 52° C. for more than, say, 15 seconds at reduced power, the heating filament power may be shut off and a panel alarm activated. This prevents the peak surface temperature from exceeding 48° C. Moreover, the average catheter surface temperature should not exceed 44° C., since the power will be switched "ON" approximately 50% of the time. Furthermore, if the average cardiac output exceeds 3.5 liters/minute, the catheter's average surface temperature will generally remain below 44° C. Thus, regulation of power to the catheter only becomes an issue when the cardiac output becomes less than about 3.5 liters/minute. However, since the power to the heating filament is reduced or shut off as the filament temperature reaches 52° C., the heating element of the invention can be made relatively fail-safe through closed-loop control of the surface temperature.

By using a power source which is a constant voltage source, an increasing catheter filament temperature can be directly detected as an increasing filament resistance which reduces the power delivered to the heating filament. In this manner, the actual current and voltage to the catheter filament may be continuously monitored. From the values of current and voltage, a delivered power may be calculated which is needed to calculate flow, and the filament resistance may be calculated and used for computing the filament temperature. Thus, at all times, the actual filament temperature is known. Preferably, the following algorithm is followed to insure that the filament temperature remains within safe limits:

(1) When the cardiac output computer starts, the delivered power to the heating filament is maintained at approximately 4 watts average power.

(2) The filament temperature is monitored for several seconds.

(3) If the peak filament temperature has not exceeded 46° C., the filament power is increased to an average power of 7.5 watts.

(4) If at any time the peak filament temperature exceeds 48° C. for more than, say, 15 seconds, the delivered filament power is reduced.

(5) If at any time the average delivered filament power is approximately 4 watts and the peak filament temperature exceeds 48° C. for more than, say, 15 seconds, the computer shuts off and displays an error message.

The cardiac output may be measured continuously by turning the heating filament on and off in a predetermined pattern and generating a characteristic thermodilution curve by a mathematical process such as cross-correlation as described in the afore-mentioned co-pending application, U.S. Ser. No. 07/510,897 to McKown et al. A detailed discussion of bolus thermodilution and pulse thermodilution techniques are described in that application.

By using an indicator dilution method in accordance with a stochastic system of the type described in the afore-mentioned related application, Ser. No. 07/510,897 to McKown et al., cardiac output may be measured in a noisy environment even when a small heat input source as herein described is used. The stochastic techniques of the type described in the afore-mentioned application are different from classical empirical techniques in that the input signal or energy is applied over a period of time, and the nature of the statistical properties of the input and output signals are of interest. Thus, during operation in accordance with this technique, the supplied heat in accordance with the present invention will produce a small temperature change in the flowing blood which is detected at the distal thermistor or thermocouple 104. Through a mathematical procedure known as cross-correlation, a scaled characteristic thermodilution "wash-out" curve is reconstructed. The cardiac output may then be calculated by measuring the area under this "wash-out" curve if the amount of heat delivered to the blood by the heating filament is also known. An indicator thermodilution equation for calculating flow is described in the afore-mentioned application.

Figure 9:
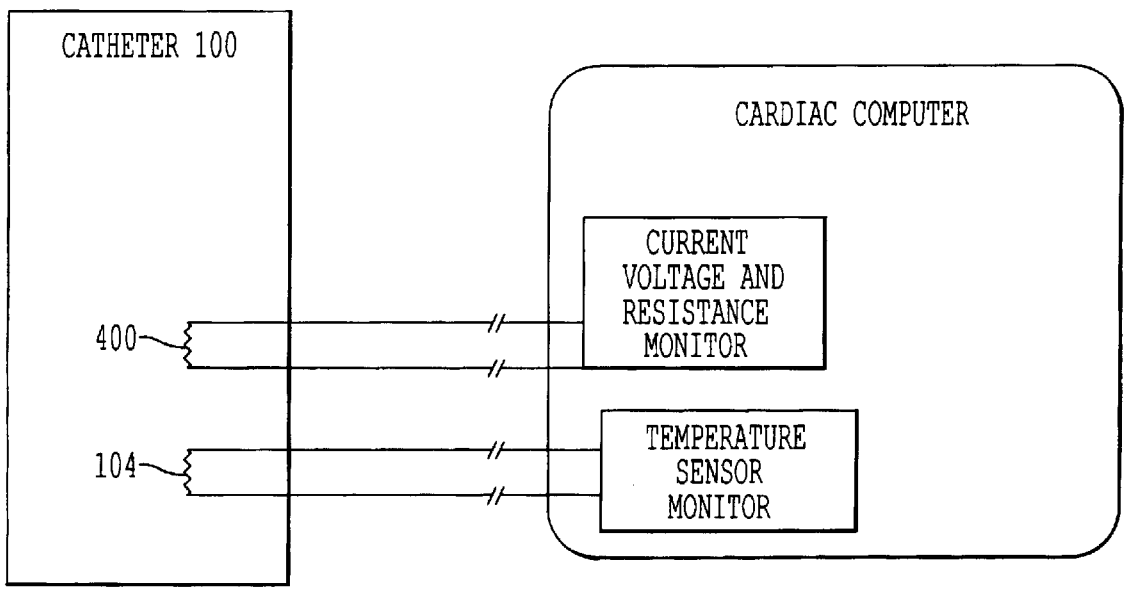
FIG. 9 illustrates a cardiac computer which monitors voltage, current, and resistant to the heating filament in accordance with a preferred embodiment of the invention.

FIG. 9 shows the elements of the cardiac computer which monitor the temperature of the thermistor or thermocouple 104 and which monitor the current, the voltage, and the resistance of the heating filament 400. The current, voltage, and resistance monitor, monitors the current and voltage of the filament 400 and monitors the resistance of the heating filament 400 based upon the monitored current and voltage.

In the calculation of cardiac output using such thermodilution techniques, it is necessary to know certain properties about the measuring transducer, such as the thermistor or thermocouple 104, and the heat application or heating filament efficiency, for in the manufacturing process it is difficult to produce either thermistors or thermocouples 104 or heating filaments 400 which uniformly have the same properties. Thus, to reduce the errors which would be introduced into the calculation of cardiac output due to these variances, it is necessary to calibrate or measure the physical properties of both the thermistor or thermocouple 104 and the heating filament 400. Since in a clinical environment each cardiac output computer may be attached over time to various pulmonary artery catheters and to eliminate the need for the user to manually transcribe these calibration numbers to the computer, a coding technique has been developed in accordance with the invention to pass the calibration information.

Prior art thermodilution catheters and pulse oximeter sensors have used resistors to code the values for thermistors or LEDs. For example, New et al. in U.S. Pat. No. 4,700,708 use a resistor to calibrate LED wavelengths on a pulse oximeter. However, the present inventors know of no previous attempt to code the filament calibration for transferring the calibration information of the heating filament solely or the calibration information of the heating filament and thermistor or thermocouple together. Thus, in accordance with the present invention, calibration of the heating element may be conducted by measuring the heater resistance at a known temperature. The catheter assembly can then use the previously calibrated thermistor or thermocouple and a built-in ohm meter to establish a calibrated reference point for the heater element. This approach has the advantage of calibrating the heater immediately prior to use in a patient at the patient's body temperature. Such an accurate calibration of heater resistance and temperature is necessary to accurately monitor heater temperature to insure patient safety.

The calibration circuit may include passive electronic components such as resistors, inductors and capacitors such that the value of the components correspond to a particular calibration value or number according to a predetermined table. On the other hand, active electronic components including numerous nonlinear components may be used such that a particular performance corresponds to a particular calibration number or value. Such calibration information is preferably stored in a memory component such as a ROM (Read Only Memory), a RAM (Random Access Memory), a nonvolatile memory device or another type of memory or digital device. The calibration information preferably includes codes that represent the filament resistance, filament efficiency, and other parameters. If properly selected, one or more electronic components may be used to encode the calibration information of the thermistor or thermocouple, such as its β value, and the filament resistance, filament efficiency and other parameters.

Thus, the calibration information for both the thermistor or thermocouple 104 and the heating filament 400 may be encoded by one or more active or passive electronic components or these values may be stored in a suitable memory device. The cardiac output computer may then decode this information and incorporate it into the calculation of cardiac output. However, this step may be eliminated if the actual appropriate software is contained in the catheter itself. For example, a memory device such as a ROM may be contained in the catheter with a portion of the software utilized by the cardiac output computer resident within it. Such information might include program segments or historical patient data. Thus, when the catheter is connected to the cardiac output computer, prior to the beginning of processing for determining the cardiac output, the software or program segment contained in the catheter memory device (ROM) may be transferred to the main software program of the cardiac output computer. This feature of the invention also provides an additional safety feature, for the cardiac output computer will not start until it has transferred the program segment and incorporated this segment into its own program.

The calibration circuitry of the type just described can be seen by way of example in FIG. 8. As should be apparent to one of ordinary skill in the art, the calibration circuit of FIG. 8 is quite different from that used in typical prior art thermodilution catheters. In particular, classic thermodilution catheters use calibration resistances which are connected in series with the thermistor or thermocouple. In such devices, the reference resistor is calibrated to match the thermistor or thermocouple for a standard temperature. In this manner, compensation for variability in the thermistors or thermocouples may be achieved. However, by using the calibration circuit of the invention where in a ROM containing calibration data is included within the connector of the catheter, such a reference resistor for calibration purposes is not needed. Such a ROM is shown as ROM 802 of connector 116 in FIG. 8.

Preferably, the software module referred to above is stored in the ROM 802 and includes such things as the format version for the calibration data, trademark information, historical patient data (such as cardiac output for the previous several hours) or whatever information is desired for controlling the cardiac output program. Thus, by placing the encoded calibration data within the ROM 802 and placing the ROM 802 on the catheter, the thermistor or thermocouple reference resistance may be eliminated. In addition, only a catheter having a ROM 802 storing the necessary information for operating the program of the cardiac output computer may be used in conjunction with the cardiac output computer to obtain the desired calculation.

Although a number of exemplary embodiments of the invention have been described in detail above, those skilled in the art will readily appreciate that many additional modifications are possible in the exemplary embodiments without materially departing from the novel teachings and advantages of this invention. For example, rather than wrapping the heating element 400 around the catheter body portion 100, the heating element may be included in the body wall portion 202 of the catheter body portion 100. In addition, the heating element 400 may be made in multiple contiguous sections, whereby by measuring the temperature of each section it is possible to determine whether one section is malfunctioning. such malfunctions could be due to filament abnormalities or due to physiologic aberrations such as clotting. The discrepancy in temperature would alert the user to a potential problem. However, such a section arrangement would require additional electrical leads, and the catheter would need to be modified accordingly. Alternatively, the heating filament of the invention may be used in conjunction with a guide wire for angioplasty, where the thermistor or thermocouple will be miniaturized and placed on the guide wire, and the heater placed upstream on the guide wire. The resulting device may then be inserted into a catheter lumen of the type described herein. In addition, the heating filament may be placed ahead of or behind balloon 102 as desired.

Accordingly, all such modifications are intended to be included within the scope of this invention as defined in the following claims.

We claim:

1. A thermodilution catheter apparatus, comprising:
   a flexible tubular catheter member adapted for introduction into a blood vessel, and
   a flexible heating filament, having a temperature coefficient of resistance whose magnitude is at least 0.001

$\Omega/\Omega$-° C., designed for heating the blood in the blood vessel for thermodilution measurements, and mounted to said flexible tubular catheter member, a sheath covering said filament so that said flexible heating filament does not contact blood when said flexible heating filament is in the blood vessel.

2. An apparatus according to claim 1, further comprising: means for measuring flexible heating filament resistance of said flexible heating filament, said means for measuring providing a flexible heating filament resistance signal corresponding to said flexible heating filament resistance.

3. An apparatus according to claim 1, further comprising blood temperature detecting means disposed along a first region of said flexible tubular catheter member for detecting blood temperature, said means for detecting blood temperature providing a blood temperature signal corresponding to the blood temperature.

4. An apparatus according to claim 3, wherein said flexible heating filament is disposed in a second region that is distinct from said first region.

5. An apparatus according to claim 1, wherein said flexible heating filament resistance varies monotonically as a of temperature.

6. An apparatus according to claim 1, wherein said flexible heating filament resistance has a temperature coefficient of resistance which is about 0.004 $\Omega/\Omega$-° C.

7. An apparatus according to claim 6 wherein said flexible heating filament is formed from an alloy that comprises nickel and iron.

8. An apparatus according to claim 7, wherein said flexible heating filament is formed from an alloy that further comprises cobalt.

9. An apparatus according to claim 1, wherein said flexible heating filament resistance has a temperature coefficient of resistance which is greater than 0.001 ohms per ohm-degree centigrade in a physiologically significant temperature range.

10. An apparatus according to claim 1, further comprising
    an electrically insulating flexible heating filament substrate, wherein said flexible heating filament is mounted on said flexible heating filament substrate.

11. An apparatus according to claim 10, wherein said flexible heating filament substrate is flexible.

12. An apparatus according to claim 10, wherein said flexible heating filament substrate is bondable to an adhesive.

13. An apparatus according to claim 10, further comprising
    a high thermal conductivity layer in contact with said flexible heating filament substrate.

14. An apparatus according to claim 13, wherein said high thermal conductivity layer comprises a metal foil layer.

15. An apparatus according to claim 10, wherein said flexible heating filament substrate comprises a member of the set consisting of polyimide film and polyester film.

16. An apparatus according to claim 10, further comprising
    an electrically insulating top layer on said flexible heating filament thereby sandwiching said flexible heating filament between said electrically insulating top layer and said flexible heating filament substrate.

17. An apparatus according to claim 1, wherein said flexible heating filament is disposed along a flexible heating filament region of said flexible tubular catheter member and further comprising
    a catheter sheath along at least said flexible heating filament region of said flexible tubular catheter member and covering said flexible heating filament.

18. An apparatus according to claim 17, wherein said catheter sheath has a smooth outer surface.

19. An apparatus according to claim 1, wherein said flexible tubular catheter member extends along a flexible tubular catheter member axis and said flexible heating filament has a cross-section with a long dimension and a short dimension and said short dimension is along a direction radiating away from said flexible tubular catheter member axis.

20. An apparatus according to claim 1, wherein said flexible heating filament extends along said flexible tubular catheter member for at least about five centimeters.

21. An apparatus according to claim 1, wherein said flexible heating filament extends along said flexible tubular catheter member for between about five and ten centimeters.

22. An apparatus according to claim 20, wherein said flexible tubular catheter member has a flexible tubular catheter member distal end and said flexible heating filament extends from about fifteen to about five centimeters from said flexible tubular catheter member distal end.

23. A thermodilution catheter apparatus, comprising:
    a flexible tubular catheter member adapted for introduction into a blood vessel; and
    a flexible heating filament, having a temperature coefficient of resistance whose magnitude is at least 0.001 $\Omega/\Omega$-° C. designed for heating the blood in the blood vessel for thermodilution measurements, and mounted to said flexible tubular catheter member so that said flexible heating filament does not contact blood when said flexible heating filament is in the blood vessel,
    wherein said flexible heating filament is disposed along a flexible heating filament region of said flexible tubular catheter member and further comprising
    a catheter sheath along at least said flexible heating filament region of said flexible tubular catheter member and covering said flexible heating filament wherein said catheter sheath comprises an adhesive.

24. A thermodilution catheter apparatus, comprising:
    a flexible tubular catheter member adapted for introduction into a blood vessel;
    a flexible heating filament, having a temperature coefficient of resistance whose magnitude is at least 0.001 $\Omega/\Omega$-° C. designed for heating the blood in the blood vessel for thermodilution measurements, and mounted to said flexible tubular catheter member so that said flexible heating filament does not contact blood when said flexible heating filament is in the blood vessel;
    wherein said flexible heating filament is disposed along a flexible heating filament region of said flexible tubular catheter member and;
    a catheter sheath along at least said flexible heating filament region of said flexible tubular catheter member and covering said flexible heating filament wherein said catheter sheath has a cylindrical outer surface with a catheter sheath diameter and a non-catheter sheath region of said catheter member that is adjacent said catheter sheath is cylindrical and has a non-catheter sheath diameter which is equal to said catheter sheath diameter.

* * * * *

UNITED STATES PATENT AND TRADEMARK OFFICE
CERTIFICATE OF CORRECTION

PATENT NO. : 6,485,430 B1
DATED : November 26, 2002
INVENTOR(S) : Michael D. Quinn and Mark L. Yelderman It is certified that error appears in the above-identified patent and that said Letters Patent is hereby corrected as shown below:

Column 19,
Line 24, after "a" please insert -- function --.

Signed and Sealed this

Eighth Day of July, 2003

JAMES E. ROGAN
*Director of the United States Patent and Trademark Office*